United States Patent
Lamola et al.

(10) Patent No.: US 6,770,600 B1
(45) Date of Patent: Aug. 3, 2004

(54) DELIVERY SYSTEMS FOR CYCLOPROPENE COMPOUNDS

(75) Inventors: Angelo Anthony Lamola, Worcester, PA (US); Richard Martin Jacobson, Chalfont, PA (US); Philip Roy Norris, North Reading, MA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/376,992

(22) Filed: Feb. 28, 2003

(51) Int. Cl.$^7$ ........................ A01N 25/10; A01N 25/28; A01N 27/00
(52) U.S. Cl. ........................................ 504/357; 504/359
(58) Field of Search .................................. 504/357, 359

(56) References Cited

U.S. PATENT DOCUMENTS

| | | | |
|---|---|---|---|
| 5,518,988 A | 5/1996 | Sisler et al. | 504/114 |
| 6,017,849 A | 1/2000 | Daly et al. | 504/114 |
| 6,313,068 B1 | 11/2001 | Daly et al. | 504/114 |
| 6,426,319 B1 | 7/2002 | Kostansek | 504/357 |
| 2002/0058592 A1 | 5/2002 | Kostansek | 504/357 |

FOREIGN PATENT DOCUMENTS

WO  02/24171  * 3/2002

* cited by examiner

*Primary Examiner*—S. Mark Clardy
(74) *Attorney, Agent, or Firm*—James C. Vouros; Thomas D. Rogerson

(57) ABSTRACT

The present invention relates to new delivery systems for cyclopropene compounds of a cyclopropene compound generator comprising at least one substrate, a material containing at least one cyclopropene compound and a release agent whereby at least one side of one substrate is coated with the material containing at least one cyclopropene compound and wherein when the material containing at least one cyclopropene compound is exposed to the release agent, a gaseous cyclopropene compound is released. The present invention also provides methods to release a cyclopropene compound from such a generator to deliver a cyclopropene compound to plants, fruits, flowers or vegetables to inhibit an ethylene response in the plants, fruits, flowers or vegetable.

13 Claims, No Drawings

DELIVERY SYSTEMS FOR CYCLOPROPENE COMPOUNDS

The present invention relates to a new delivery system for cyclopropene compounds whereby cyclopropene compounds can be delivered in a controlled manner. The delivery system or cyclopropene compound generator comprises at least one substrate, a material containing at least one cyclopropene compound and a release agent whereby at least one side of one substrate is coated with the material containing at least one cyclopropene compound and wherein when the material containing at least one cyclopropene compound is exposed to the release agent, a gaseous cyclopropene compound is released. The cyclopropene compound generator can be in the form of a cartridge, preferably a self contained cartridge, which provides a convenient means for delivering cyclopropene compounds to flowers, fruits, plants and vegetables in order to preserve their same quality as when they were picked. Such cyclopropene compounds and their derivatives, such as methylcyclopropene, are capable of inhibiting the ethylene response in flowers, fruits, plants and vegetables. The cyclopropene compound generator is particularly useful where the flowers, fruits, plants or vegetables are stored in areas, such as railroad box cars, tractor trailer containers or land/sea containers because the cyclopropene compound generator eliminates the need for cumbersome mixing equipment, delivers a fixed dosage appropriate for the container's content and cubic volume and significantly reduces any waste product.

It is well known that ethylene can cause the premature death of plants or plant parts including, for example, flowers, leaves, fruits, and vegetables through binding with certain receptors in the plant. Ethylene also promotes leaf yellowing and stunted growth as well as premature fruit, flower, and leaf drop. Because of these ethylene-induced problems, very active and intense research presently concerns the investigation of ways to prevent or reduce the deleterious effects of ethylene on plants. U.S. Pat. No. 5,518,988 discloses the use of cyclopropene and its derivatives, including methylcyclopropene, as effective blocking agents for ethylene binding. However, a major problem with these compounds is that they are typically unstable gases which present explosive hazards when compressed, making them difficult to deliver.

As a solution to these problems, U.S. Pat. No. 6,017,849 discloses a method of incorporating these gaseous compounds into a molecular encapsulation agent complex in order to stabilize their reactivity and thereby provide a convenient and safe means of storing, transporting and applying or delivering the active compounds to plants, flowers, fruits or vegetables. For the most active cyclopropene derivative disclosed in U.S. Pat. No. 5,518,988, 1-methylcyclopropene, the preferred molecular encapsulation agent is a cyclodextrin, with α-cyclodextrin being the most preferred. The application or delivery of these active compounds to plants, flowers, fruits or vegetables is accomplished by simply adding water to the molecular encapsulation agent complex. The complex is prepared according to the methods disclosed in U.S. Pat. No. 6,017,849 which provides the material in the form of a powder.

The bulk or encapsulated form of 1-methylcyclopropene/α-cyclodextrin complexes noted above can be made to release the 1-methylcyclopropene very quickly. However, in order to accomplish this release, large amounts of water are required, at least ten times and preferably twenty times the weight of the 1-methylcyclopropene/α-cyclodextrin complex. In addition, the vessel containing the water must be kept upright to avoid spillage. It would be advantageous to accomplish complete release of the cyclopropene compound from the complex using a minimal amount of water or release agent and where the orientation of the container does not matter. This would allow a user to treat plants, flowers, fruits, or vegetables with the gaseous cyclopropene compound directly in shipping containers, rather than a large treatment container, chamber, or room.

U.S. patent application Ser. No. 09/957,752 attempts to solve this problem by mixing the powdered complex with a water absorbent material. Less water is utilized to release the cyclopropene compound but, in one embodiment, excess water is still needed and therefore leads to an aqueous byproduct once the cyclopropene compound generation is complete. This byproduct has to be disposed of properly according to regulatory and environmental standards. In another embodiment, a sachet filled with the cyclopropene compound complex can simply be exposed to a humid atmosphere which acts as the release agent. Although this appears to eliminate the problem of an unwanted byproduct, it raises some additional problems such as having to control the humidity of the environment in the container to be able to deliver the optimum amount of cyclopropene compound in a reasonable amount of time.

We have found a way to simplify the process for the release of a cyclopropene compound, substantially reduce the amount of unwanted byproduct to comply with environmental regulations and be able to deliver an accurate dosage amounts appropriate for a container's content and cubic volume without having to control the container's environment. One embodiment of the present invention is a cyclopropene compound generator comprising at least one substrate, a material containing at least one cyclopropene compound and a release agent whereby at least one side of one substrate is coated with a material containing at least one cyclopropene compound and wherein when the substrate coated with the material containing at least one cyclopropene compound is exposed to the release agent, a gaseous cyclopropene compound is released.

The release agent can be contained in a reservoir whereby the substrate coated with the material containing at least one cyclopropene compound is pulled through, over or under the reservoir to expose the substrate coated with the material containing at least one cyclopropene compound to the release agent. A suitable reservoir can be in any form, such as a bath or chamber with an inlet to allow the substrate coated with the material containing at least one cyclopropene compound to enter and an outlet for the substrate with the coating material containing at least one cyclopropene compound to exit, to a porous material such as a sponge. The release agent can also be contained in a rupturable container or pod. When utilizing a pod, it is preferable that each section of the substrate coated with the material containing at least one cyclopropene compound contains at least one pod. The substrate coated with the material containing at least one cyclopropene compound passes through a pressure applying assembly, such as a pair of rollers, that rupture the pod and spread the release agent to initiate the release of gaseous cyclopropene compound. Alternately, a second substrate can be used that is coated with the release agent whereby the substrate with the coating material containing at least one cyclopropene compound and the substrate coated with the release agent are contacted together to cause the release of a gaseous cyclopropene compound. When utilizing this technique of two substrates, one substrate with the coating material containing at least one cyclopropene compound and one substrate coated with the release agent, it is preferable the material for at least one of the substrates be porous to aid in the release of the gaseous cyclopropene compound.

It is preferable this cyclopropene compound generator be in the form of a cartridge, preferable a self contained cartridge. The substrate or substrates are stored in the cartridge and can be either coated prior to being placed in the cartridge or the cartridge can be configured such that the substrate or substrates are uncoated and the coating material containing at least one cyclopropene compound and/or the release agent are stored in separate portions of the cartridge. This configuration provides for the coating of the substrates immediately prior to use. It is preferable however to utilize at least one substrate precoated with the material containing at least one cyclopropene compound prior to placing it in the cartridge.

Essentially, the cartridge serves as a dispenser for the substrate or substrates. When utilizing a substrate where the material containing at least one cyclopropene compound has already been applied to the substrate and the release agent is contained is a separate reservoir, the substrate coated with the material containing at least one cyclopropene compound can be pulled or removed from the cartridge such that it is passed through, under or by the portion of the cartridge containing the release agent. The release agent is applied in a controlled manner to the substrate coated with the material containing at least one cyclopropene compound, causing a gaseous cyclopropene compound to begin to be released. For an uncoated substrate, when pulling or removing the substrate from the cartridge, the substrate also passes through, under or by a portion of the cartridge containing the material containing at least one cyclopropene compound. Either the material containing at least one cyclopropene compound or the release agent can be applied first to the substrate, followed by application of the other. It is preferable to apply the material containing at least one cyclopropene compound first and even more preferable to have a substrate previously coated with the material containing at least one cyclopropene compound in the cartridge.

In the alternative, when utilizing two substrates, one for the material containing at least one cyclopropene compound and one for the release agent, both can be uncoated, both can be coated or one coated and one uncoated prior to placing in the cartridge. If a substrate is uncoated when placed in the cartridge, then it would need to be coated by passing through, by or under a reservoir containing the appropriate coating material, whether the material containing at least one cyclopropene compound or the release agent. When utilizing two substrates, it is preferable they both be coated prior to placing in the cartridge.

Once pulled or removed from the cartridge, the substrate coated with the material containing at least one cyclopropene compound on at least one side and release agent can remain attached to the cartridge or can be separated from the cartridge and hung or set in any location in the closed area. Similarly, if two substrates are used, one with the material containing at least one cyclopropene compound on at least one side and one with the release agent on at least one side, the two substrates can be contacted with each other such that the release agent acts to release a gaseous cyclopropene compound and can remain attached to the cartridge or can be separated from the cartridge and hung or set in any location in the closed area.

It is preferable for the substrate or substrates, whether coated or uncoated, to be contained in the cartridge in a continuous roll. Where two substrates are used, it is preferable there be two separate continuous rolls of substrate whereby when the substrates are dispensed from the cartridge, the two substrates are brought into contact with each other as, for example, a laminated film. In addition, the substrate or substrates can be folded in such a way in the cartridge, such as for example accordion style, that when they are dispensed they can be placed, set or tossed in any location to expose maximum surface area.

Another advantage of the present invention is that the dosage level for a particular content or cubic volume can be controlled by controlling the length or amount of coated substrate or substrates dispensed from the cartridge. When dispensing the substrate or substrate, it is preferable to have a portion with no coating that corresponds to the area where the substrate will be cut or torn from the cartridge. This further eliminates waste due to any unused, coated portion.

Because of the fixed amount of release agent being applied to the fixed amount of material containing at least one cyclopropene compound, the reaction to regenerate the gaseous cyclopropene compound can be carried out to completion in a reasonable period of time, such as the total storage time of the flowers, fruits, plants or vegetables.

The present invention is, therefore, a cyclopropene compound generator comprising at least one substrate, a material containing at least one cyclopropene compound and a release agent wherein at least one substrate is coated with the material containing at least one cyclopropene compound and when the material containing at least one cyclopropene compound is exposed to a release agent, a gaseous cyclopropene compound is released. The material containing at least one cyclopropene compound comprises a cyclopropene of the formula:

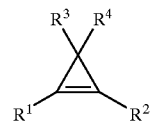

wherein:

1) each $R^1$, $R^2$, $R^3$, and $R^4$ is independently a group of the formula:

wherein:

i) n is an integer from 0 to 12;

ii) each L is independently selected from a member of the group D1, D2, E or J wherein:
D1 is of the formula:

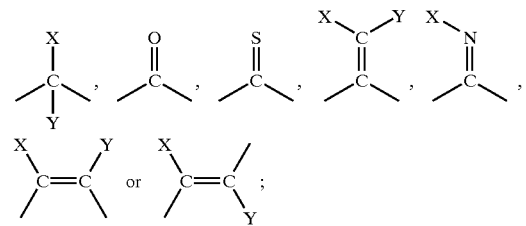

D2 is of the formula:

[chemical structures]

E is of the formula:

[chemical structures]

J is of the formula:

[chemical structures]

wherein:
A) each X and Y is independently a group of the formula:

—(L)$_m$—Z;

and

B) m is an integer from 0 to 8; and
C) no more than two E groups are adjacent to each other and no J groups are adjacent to each other;
iii) each Z is independently selected from:
  A) hydrogen, halo, cyano, nitro, nitroso, azido, chlorate, bromate, iodate, isocyanato, isocyanido, isothiocyanato, pentafluorothio, or
  B) a group G, wherein G is an unsubstituted or substituted; unsaturated, partially saturated, or saturated; monocyclic, bicyclic, tricyclic, or fused; carbocyclic or heterocyclic ring system wherein;
    1) when the ring system contains a 3 or 4 membered heterocyclic ring, the heterocyclic ring contains 1 heteroatom;
    2) when the ring system contains a 5, or more, membered heterocyclic ring or a polycyclic heterocyclic ring, the heterocyclic or polycyclic heterocyclic ring contains from 1 to 4 heteroatoms;
    3) each heteroatom is independently selected from N, O, and S;
    4) the number of substituents is from 0 to 5 and each substituent is independently selected from X;
2) the total number of non-hydrogen atoms in each compound is 50 or less; and its enantiomers, stereoisomers, salts, and mixtures thereof.

For the purposes of this invention, in the structural representations of the various L groups each open bond indicates a bond to another L group, a Z group, or the cyclopropene moiety. For example, the structural representation

[chemical structure]

indicates an oxygen atom with bonds to two other atoms; it does not represent a dimethyl ether moiety.

As used herein, the term "halo" means fluorine, chlorine, bromine, and iodine.

Preferably, the number of non-hydrogen atoms in each compound is less than 25. More preferably, the number of non-hydrogen atoms in each compound is less than 20. Even more preferably, the number of non-hydrogen atoms in each compound is less than 13. Most preferably, the number of non-hydrogen atoms in the compound is less than 7.

Preferably, two of $R^1$, $R^2$, $R^3$, and $R^4$ are hydrogen. More preferably, $R^1$ and $R^2$ are hydrogen or $R^3$ and $R^4$ are hydrogen. Even more preferably, $R^2$, $R^3$, and $R^4$ are hydrogen or $R^1$, $R^2$, and $R^3$ are hydrogen. Most preferably, $R^2$, $R^3$, and $R^4$ are hydrogen.

Preferably, $R^1$ is $(C_1-C_{10})$ alkyl and $R^2$, $R^3$, and $R^4$ are hydrogen. More preferably, $R^1$ is $(C_1-C_8)$ alkyl and $R^2$, $R^3$, and $R^4$ are hydrogen. Even more preferably $R^1$ is $(C_1-C_4)$ alkyl and $R^2$, $R^3$, and $R^4$ are hydrogen. Most preferably, $R^1$ is methyl and $R^2$, $R^3$, and $R^4$ are hydrogen.

Typical $R^1$, $R^2$, $R^3$, and $R^4$ groups include, for example: alkenyl, alkyl, alkynyl, acetylaminoalkenyl, acetylaminoalkyl, acetylaminoalkynyl, alkenoxy, alkoxy, alkynoxy, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyl, alkylcarbonyloxyalkyl, alkyl(alkoxyimino)alkyl, carboxyalkenyl, carboxyalkyl, carboxyalkynyl, dialkylamino, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylphosphonato, dialkylphosphato, dialkylthiophosphato, dialkylaminoalkyl, alkylsulfonylalkyl, alkylthioalkenyl, alkylthioalkyl, alkylthioalkynyl, dialkylaminosulfonyl, haloalkylthioalkenyl, haloalkylthioalkyl, haloalkylthioalkynyl, alkoxycarbonyloxy; cycloalkenyl, cycloalkyl, cycloalkynyl, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, dicycloalkylamino, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, dicycloalkylaminosulfonyl, haloalkylthiocycloalkenyl, haloalkylthiocycloalkyl, haloalkylthiocycloalkynyl; aryl, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, haloalkylthioaryl; heteroaryl, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, heteroarylthioalkyl, diheteroarylaminosulfonyl, haloalkylthioheteroaryl; heterocyclyl, alkenylheteroycycyl, alkylheteroycycyl, alkynylheteroycycyl, acetylaminoheterocyclyl, heterocyclyloxy, alkoxyalkoxyheterocyclo, alkoxyheterocyclyl, alkoxycarbonylheterocyclyl, heterocyclylcarbonyl, alkylcarbonyloxyheterocyclyl, carboxyheterocyclyl, diheterocyclylamino, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, diheterocyclylaminosulfonyl, haloalkyllthioheterocyclyl; hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

Typical G groups include, for example: saturated or unsaturated cycloalkyl, bicyclic, tricyclic, polycyclic, saturated or unsaturated heterocyclic, unsubstituted or substituted phenyl, naphthyl, or heteroaryl ring systems such as, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol -1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butyl-pyridin-2-yl, 4-bromo-pyridin-2-yl, 5-carboe,thoxy-pyridin-2-yl, 6-methoxyethoxy-pyridin-2-yl.

To apply the material containing at least one cyclopropene compound to the substrate it is preferable to form a complex of the cyclopropene compound with agents such as cyclodextrins, crown ethers, polyoxyalkylenes, polysiloxanes, and zeolites. More preferred complexing agents include α-cyclodextrin, β-cyclodextrin, and γ-cyclodextrin. The most preferred complexing agent, particularly when the cyclopropene compound is 1-methylcyclopropene, is α-cyclodextrin. The most preferred complexing agent will vary depending upon the size of the R substituent. However, as one skilled in the art will appreciate, any cyclodextrin or mixture of cyclodextrins, cyclodextrin polymers as well as modified cyclodextrins can also be utilized pursuant to the present invention. Cyclodextrins are available from Wacker Biochem Inc., Adrian, Mich. or Cerestar USA, Hammond, Ind., as well as other vendors.

The materials containing at least one cyclopropene compound of the present invention are prepared by contacting the cyclopropene compound with a solution or slurry of a complexing agent and then isolating the material, again using general processes disclosed in U.S. Pat. No. 6,017, 849. In the case of 1-methylcyclopropene, 1-methylcyclopropene gas is bubbled through a solution of α-cyclodextrin in water from which the complex first precipitates and is then isolated by filtration.

It is often desirable to include in the material containing at least one cyclopropene compound, one or more adjuvants or excipients, such as extenders, binders, lubricants, surfactants and/or dispersants, wetting agents, spreading agents, dispersing agents, stickers, adhesives, defoamers, thickeners, emulsifying agents and the like.

A wide variety of water absorbent materials may be used in the material containing at least one cyclopropene compound. These include one or more organic materials such as superabsorbent polymers, such as, for example, sodium polyacrylate (crosslinked), polysaccharides, acrylamide/acrylate copolymers, and carboxymethylcellulose; one or more inorganic deliquescent compounds such as, for example, calcium chloride, magnesium chloride, lithium chloride, zinc chloride, magnesium nitrate, and aluminum nitrate; and combinations and mixtures thereof. To ease in the application of the material containing at least one cyclopropene compound and to insure it remains fixed to the substrate, the material containing at least one cyclopropene compound can also contain a gelling agent, including naturally occurring compounds such as carrageenan and gelatin.

In addition, either the release agent or the material containing at least one cyclopropene compound can include a gas evolving material such as a material that generates carbon dioxide, oxygen, nitrogen or hydrogen. These materials can be for example, sodium bicarbonate, potassium bicarbonate or calcium carbonate. Optionally, these gas generating materials can be coated with a polymeric substance to better control the rate of the release of the cyclopropene compound. In addition, to further enhance the release of a gas evolving material, an acidic compound can be added to either the release agent or the material containing at least one cyclopropene compound, preferably the one not containing the gas evolving material.

The coating material can be coated onto the substrate prior to the substrate being placed in the cyclopropene compound generator or, alternatively, the coating material may be placed in a water impermeable container in the cyclopropene compound generator for application to the substrate. The formulation of the material containing at least one cyclopropene compound and the formulation of the release agent will depend on how it is used.

The substrate to be coated with either the material containing at least one cyclopropene compound or the release agent can be in any form, such as a flexible film, web, nonwoven or woven material or a foam. The substrate can be porous or nonporous and can be made of materials such as plastic, paper or fabric from either natural or synthetic fiber. When utilizing a substrate for the release agent and a substrate for the material containing at least one cyclopropene compound it is not essential to utilize the same types of substrates. Different types of substrates can be used, one type for the release agent and one type for the material containing at least one cyclopropene compound, however it is preferable for at least one of the substrates to be porous to aid in the release of gaseous cyclopropene compound.

The release agent for the cyclopropene compound can be any agent capable of causing a gaseous cyclopropene compound to be generated from the material containing at least one cyclopropene compound. For example, the release agent can be water or water containing, an alcohol such as methanol, an acid such as citric acid, a displacing agent such as dodecyltrimethylammonium chloride, or combinations thereof. In addition, the release agent can contain other adjuvants such as a thickener, defoamer or gelling agent. It is preferable, particularly where the release agent is applied to a substrate, for the release agent to be in the form of a gel. Any gelling agent can be used, including naturally occurring compounds such as carrageenan and gelatin.

As used herein, all percentages are percent by weight and all parts are parts by weight, unless otherwise specified, and are inclusive and combinable. All ratios are by weight and all ratio ranges are inclusive and combinable. All molar ranges are inclusive and combinable.

Some embodiments of this invention are illustrated by the following examples:

Release Agent Substrate—A

A solution of 3.0% hydroxypropylmethylcellulose in water is prepared by mixing the hydroxypropylmethylcellulose in water at elevated temperature. The solution is kept hot to prevent gelling and is then hot coated with a coating knife onto a substrate of polypropylene film 11 m long, 10.2 cm wide and 0.50 mm thick. The gap on the knife is set to yield a coating with a thickness of 0.30 mm. The coated substrate is allowed to cool to room temperature.

Release Agent Substrate—B

A solution of 3.0% kappa-carrageenan, 8.0% citric acid, and 3.0% dodecyltrimethylammonium chloride in water is prepared at elevated temperature. The solution is kept hot to prevent gelling and is then coated with a coating knife onto a substrate of polyester film 11 m long, 10.2 cm wide and 0.25 mm thick. The gap on the knife is set to yield a coating with a thickness of 0.30 mm. The coated substrate is allowed to cool to room temperature.

Release Agent Substrate—C

A solution of 4.0% gelatin, 8.0% citric acid, and 3.0% dodecyltrimethylammonium chloride in water is prepared at elevated temperature. The solution is kept hot to prevent gelling and is coated with a coating knife onto a substrate of polyester film 11 m long, 10.2 cm wide and 0.40 mm thick. The gap on the knife is set to yield a coating with a thickness of 0.50 mm. The coated substrate is allowed to cool to room temperature.

Release Agent Substrate—D

A solution of 3.0% kappa-carrageenan, 8.0% citric acid, and 3.0% dodecyltrimethylammonium chloride in water is prepared at elevated temperature. The solution is kept hot to prevent gelling and is coated with a coating knife onto a substrate of polyethylene film 11 m long, 2.2 cm wide and 0.33 mm thick. The gap on the knife is set to yield a coating with a thickness of 0.30 mm. The coated substrate is allowed to cool to room temperature.

Release Agent Solution—E

A solution of 1.0% kappa-carrageenan, 8.0% citric acid, and 3.0% dodecyltrimethylammonium chloride in water is prepared at elevated temperature. The solution is allowed to cool to room temperature, forming a gel.

Cyclopropene Compound Substrate—I

A mixture of 22.7 g of 1-methylcyclopropene/$\alpha$-cyclodextrin complex (4.4% 1-MCP w/w), 15.6 g of sodium bicarbonate, 2.0 g of polyvinylpyrrolidinone, and 59 g of carboxymethylcellulose sodium salt is prepared. This solution is then pressure coated onto a porous paper substrate 10.0 m long, 10.0 cm wide and 0.43 mm thick. The coating is 0.10 mm thick and weighs 140 g per $m^2$.

Cyclopropene Compound Substrate—II

A mixture of 34.2 g of 1-methylcyclopropene/$\alpha$-cyclodextrin complex (4.4% 1-MCP w/w), 23.5 g of sodium bicarbonate, 2.0 g of polyvinylpyrrolidinone, and 40.3 g of microcrystalline cellulose is prepared. This solution is then pressure coated onto a porous polyethylene film strip 10.0 m long, 10.0 cm wide and 0.22 mm thick. The coating is 0.20 mm thick and weighs 280 g per $m^2$.

Cyclopropene Compound Substrate—III

A mixture of 22.7 g of 1-methylcyclopropene/$\alpha$-cyclodextrin complex (4.4% 1-MCP w/w), 15.6 g of sodium bicarbonate, 2.0 g of polyvinylpyrrolidinone, and 59 g of carboxymethylcellulose sodium salt is prepared. This solution is then pressure coated onto a non-woven polyethylene substrate 10.0 m long, 2.0 cm wide and 0.24 mm thick. The coating is measured and is 0.10 mm thick and weighs 140 g per $m^2$.

Cyclopropene Compound Substrate—IV

A mixture of 22.7 g of 1-methylcyclopropene/$\alpha$-cyclodextrin complex (4.4% 1-MCP w/w), 15.6 g of sodium bicarbonate, 2.0 g of polyvinylpyrrolidinone, 10 g of calcium chloride and 49 g of microcrystalline cellulose is suspended in 50 ml of methylene chloride. This suspension is slurry coated onto a non-woven polyethylene strip 10.0 m long, 2.0 cm wide and 0.83 mm thick. After air drying coating is measured and is 0.16 mm thick and weighs 140 g per $m^2$.

EXAMPLE 1

A 10 cm length of Substrate I is roller contacted with a 11 cm length of Release Agent Substrate A and is placed in a 10.0 $m^3$ chamber. The chamber is at standard atmospheric pressure, temperature and humidity. Samples of the atmosphere are taken and are analyzed by gas chromatography to determine the concentration 1-MCP released. The results are shown in Table 1

TABLE 1

| Time in minutes | Chamber concentration (ppb v/v) |
| --- | --- |
| 10 | 45 |
| 20 | 183 |
| 30 | 389 |
| 40 | 458 |
| 50 | 522 |
| Theoretical maximum | 580 |

EXAMPLE 2

A 10 cm length of Substrate I is roller contacted with a 11 cm length of Release Agent Substrate B and is placed in a 10.0 $m^3$ chamber. The chamber is at standard atmospheric pressure, temperature and humidity. Samples of the atmosphere are taken and are analyzed by gas chromatography to determine the centration 1-MCP released. The results are shown in Table 2.

TABLE 2

| Time in minutes | Chamber concentration (ppb v/v) |
|---|---|
| 10 | 148 |
| 20 | 293 |
| 30 | 498 |
| 40 | 578 |
| 50 | 579 |
| Theoretical maximum | 580 |

EXAMPLE 3

A 10 cm length of Substrate II is roller contacted with a 11 cm length of Release Agent Substrate C and is placed in a 10.0 m$^3$ chamber. The chamber is at standard atmospheric pressure, temperature and humidity. Samples of the atmosphere are taken and are analyzed by gas chromatography to determine the concentration 1-MCP released. The results are shown in Table 3.

TABLE 3

| Time in minutes | Chamber concentration (ppb v/v) |
|---|---|
| 10 | 253 |
| 20 | 1047 |
| 30 | 1657 |
| 40 | 1723 |
| 50 | 1744 |
| Theoretical maximum | 1749 |

EXAMPLE 4

A 30 cm length of Substrate II is drawn through a bath containing Release Agent Solution E and is placed in a 106 m$^3$ chamber. The chamber is at standard atmospheric pressure, temperature and humidity. Samples of the atmosphere are taken and are analyzed by gas chromatography to determine the concentration 1-MCP released. The results are shown in Table 4.

TABLE 4

| Time in minutes | Chamber concentration (ppb v/v) |
|---|---|
| 10 | 887 |
| 20 | 2005 |
| 30 | 4111 |
| 40 | 4832 |
| 50 | 4991 |
| Theoretical maximum | 4996 |

EXAMPLE 5

A standard 48 foot (96 m$^3$) refrigerated truck trailer is loaded with 48 pallets of apples. A 55 cm length of Cyclopropene Compound Substrate II is roller contacted with a 57 cm length of Release Agent Substrate C and is placed in the truck trailer and the rear door of the truck is closed. Samples of the atmosphere in the trailer are taken and analyzed by gas chromatography to determine the concentration 1-MCP released. The results are shown in Table 5.

TABLE 5

| Time in minutes | Trailer concentration (ppb v/v) |
|---|---|
| 10 | 249 |
| 20 | 526 |
| 30 | 784 |
| 40 | 903 |
| 50 | 997 |
| Theoretical maximum | 1000 |

EXAMPLE 6

A 25 mm by 25 mm square of Cyclopropene Compound Substrate II is cut using scissors. This square contains 175 mg of coating containing 1.5% 1-MCP (2.625 mg 1-MCP). The square is placed in a 122 ml vial and a septum is crimped onto the vial. 5.0 g of water is added and the vial is agitated for 30 minutes. Gas chromatographic analysis of the air in the vial shows a concentration of 9998 ppm indicating full release of the 1-MCP.

In a similar manner the used substrate of Example 3 is taken and the residual level of 1-MCP is measured gas chromatographic analysis of the air in the vial shows a concentration of 6 ppm indicating 0.06% of the original 1-MCP remains.

We claim:

1. A cyclopropene compound generator comprising at least one substrate, a material containing at least one cyclopropene compound and a release agent whereby at least one side of one substrate is coated with the material containing at least one cyclopropene compound and wherein when the material containing at least one cyclopropene compound is exposed to the release agent, a gaseous cyclopropene compound is released.

2. The cyclopropene compound generator of claim 1 comprising a cartridge wherein at least one substrate is stored in one portion of the cartridge and the release agent is stored in a separate portion of the cartridge and wherein the substrate has been coated with material containing at least one cyclopropene compound.

3. The cyclopropene compound generator of claim 1 wherein the release agent is selected from the group consisting of water, an acid, an alcohol, a displacing agent and combinations thereof.

4. The cyclopropene compound generator of claim 1 wherein the release agent is in the form of a gel.

5. The cyclopropene compound generator of claim 1 wherein the release agent is contained in a rupturable container.

6. The cyclopropene compound generator of claim 1 containing at least two substrates, one substrate with the coating material containing at least one cyclopropene compound and one substrate coated with the release agent, wherein when the substrates are dispensed from the cyclopropene compound generator they are contacted together and wherein at least one of the substrates is porous.

7. The cyclopropene compound generator of claim 1 wherein the material containing at least one cyclopropene compound comprises a compound of the formula:

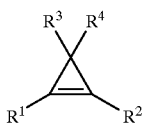

wherein:

1) each $R^1$, $R^2$, $R^3$, and $R^4$ is independently a group of the formula:

wherein:

i) n is an integer from 0 to 12;

ii) each L is independently selected from a member of the group D1, D2, E or J wherein:
D1 is of the formula:

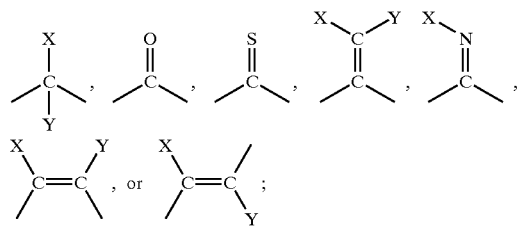

D2 is of the formula;

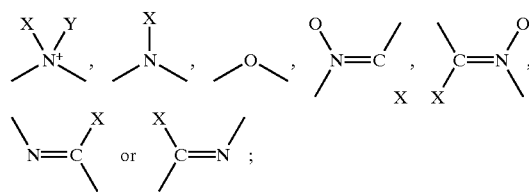

E is of the formula:

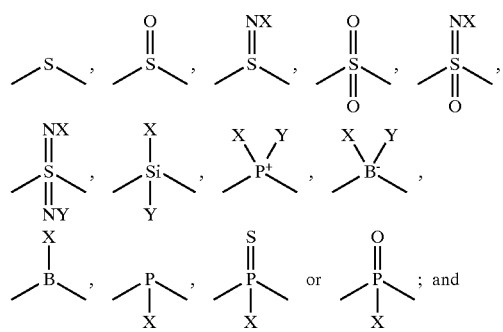

J is of the formula:

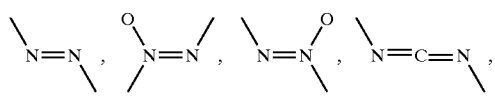

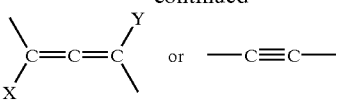

wherein:

A) each X and Y is independently a group of the formula:

and

B) m is an integer from 0 to 8; and

C) no more than two E groups are adjacent to each other and no J groups are adjacent to each other;

iii) each Z is independently selected from:
A) hydrogen, halo, cyano, nitro, nitroso, azido, chlorate, bromate, iodate, isocyanato, isocyanido, isothiocyanato, pentafluorothio, or B) a group G, wherein G is an unsubstituted or substituted; unsaturated, partially saturated, or saturated; monocyclic, bicyclic, tricyclic, or fused; carbocyclic or heterocyclic ring system wherein;
1) when the ring system contains a 3 or 4 membered heterocyclic ring, the heterocyclic ring contains 1 heteroatom;
2) when the ring system contains a 5, or more, membered heterocyclic ring or a polycyclic heterocyclic ring, the heterocyclic or polycyclic heterocyclic ring contains from 1 to 4 heteroatoms;
3) each heteroatom is independently selected from N, O, and S;
4) the number of substituents is from 0 to 5 and each substituent is independently selected from X;

2) the total number of non-hydrogen atoms in each compound is 50 or less; and its enantiomers, stereoisomers, salts, and mixtures thereof.

8. The composition of claim 7, wherein $R^1$ is $(C_1-C_{10})$ alkyl and $R^2$, $R^3$, and $R^4$ are hydrogen.

9. The composition of claim 7, wherein $R^1$ is $(C_1-C_4)$ alkyl and $R^2$, $R^3$, and $R^4$ are hydrogen.

10. The composition of claim 7, wherein $R^1$ is methyl and $R^2$, $R^3$, and $R^4$ are hydrogen.

11. The cyclopropene compound generator of claim 4 wherein the material containing at least one cyclopropene compound comprises a cyclodextrin or a mixture of cyclodextrins.

12. A method of releasing at least one cyclopropene compound comprising coating at least one side of a substrate with a material containing at least one cyclopropene compound and exposing the coated substrate to a release agent wherein a gaseous cyclopropene compound is released.

13. A method to deliver a cyclopropene compound to a plant, fruit, flower or vegetable to inhibit an ethylene response in the plant, fruit, flower or vegetable, comprising the steps of coating at least one side of a substrate with a material containing at least one cyclopropene compound and exposing the substrate coated with the material containing at least one cyclopropene compound to a release agent wherein a gaseous cyclopropene compound is released, in the presence of the plant, fruit, flower or vegetable.

* * * * *